US00PP25246P2

(12) United States Plant Patent
Duyndam

(10) Patent No.: US PP25,246 P2
(45) Date of Patent: Jan. 27, 2015

(54) ***LEUCOTHOE* PLANT NAMED 'LITTLE FLAMES'**

(50) Latin Name: ***Leucothoe* hybrid**
Varietal Denomination: Little Flames

(71) Applicant: Leo Duyndam, Zundert (NL)

(72) Inventor: Leo Duyndam, Zundert (NL)

(73) Assignee: Ron Van Opstal Holding BV, Zundert (NL)

( * ) Notice: Subject to any disclaimer, the term of this patent is extended or adjusted under 35 U.S.C. 154(b) by 186 days.

(21) Appl. No.: 13/815,376

(22) Filed: Feb. 26, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Penny J. Aguirre

(57) ABSTRACT

A new cultivar of *Leucothoe*, 'Little Flames', that is characterized by its dwarf, dense plant habit, its narrow leaves, its new growth with bright red leaves, petioles, and stems, and its cold hardiness at least to U.S.D.A. Zone 5.

2 Drawing Sheets

Botanical classification: *Leucothoe* hybrid.
Variety denomination: 'Little Flames'.

BACKGROUND OF THE INVENTION

The present invention relates to a new and distinct cultivar of *Leucothoe* of hybrid origin. The parent plant is thought to be a hybrid of *Leucothoe fontanesiana* and *Leucothoe axillaris*, however the cross cannot be confirmed. The new *Leucothoe* will hereafter by its cultivar name, 'Little Flames'. 'Little Flames' is a new cultivar of evergreen shrub grown for use as an ornamental landscape plant.

The new cultivar was discovered by the Inventor in fall of 2007 as a naturally occurring branch mutation of *Leucothoe* 'Zeblid' (U.S. Plant Pat. No. 5,195) that was growing in a container in Zundert, The Netherlands.

Asexual propagation of the new cultivar was first accomplished by the Inventor using softwood stem cuttings in summer of 2008 in Zundert, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Flames' as a unique cultivar of *Leucothoe*.

1. 'Little Flames' exhibits a dwarf, dense plant habit.
2. 'Little Flames' exhibits narrow leaves.
3. 'Little Flames' exhibits new growth with bright red leaves, petioles, and stems.
4. 'Little Flames' is cold hardy at least to U.S.D.A. Zone 5.

'Zeblid', the parent of 'Little Flames', is similar to 'Little Flames' in plant habit and in having brightly colored new growth, however 'Zeblid' differs from 'Little Flames' in having new growth that is lighter red. 'Little Flames' can be most closely compared to cultivars that are thought to be cultivars of the same hybrid species; 'Zebekot' (U.S. Plant Pat. No. 5,224) and 'Zebonard' (U.S. Plant Pat. No. 5,229). Both 'Zebekot' and 'Zebonard' are similar to 'Little Flames' in plant habit and cold hardiness. 'Zebekot' differs from 'Little Flames' in having leaves that are more lanceolate in shape and in having new foliage that is less red in color. 'Zebonard' differs from 'Little Flames' in having leaves that are wider and in having new foliage that is less red in color.

BRIEF DESCRIPTION OF THE DRAWING

The accompanying colored photographs illustrate the overall appearance and distinct characteristics of the new cultivar. The plant in the photographs is about 3 year in age as grown outdoors in a 12-liter container in Zundert, The Netherlands.

The photograph in FIG. 1 provides an overall view of the plant habit of 'Little Flames'.

Figure 1:
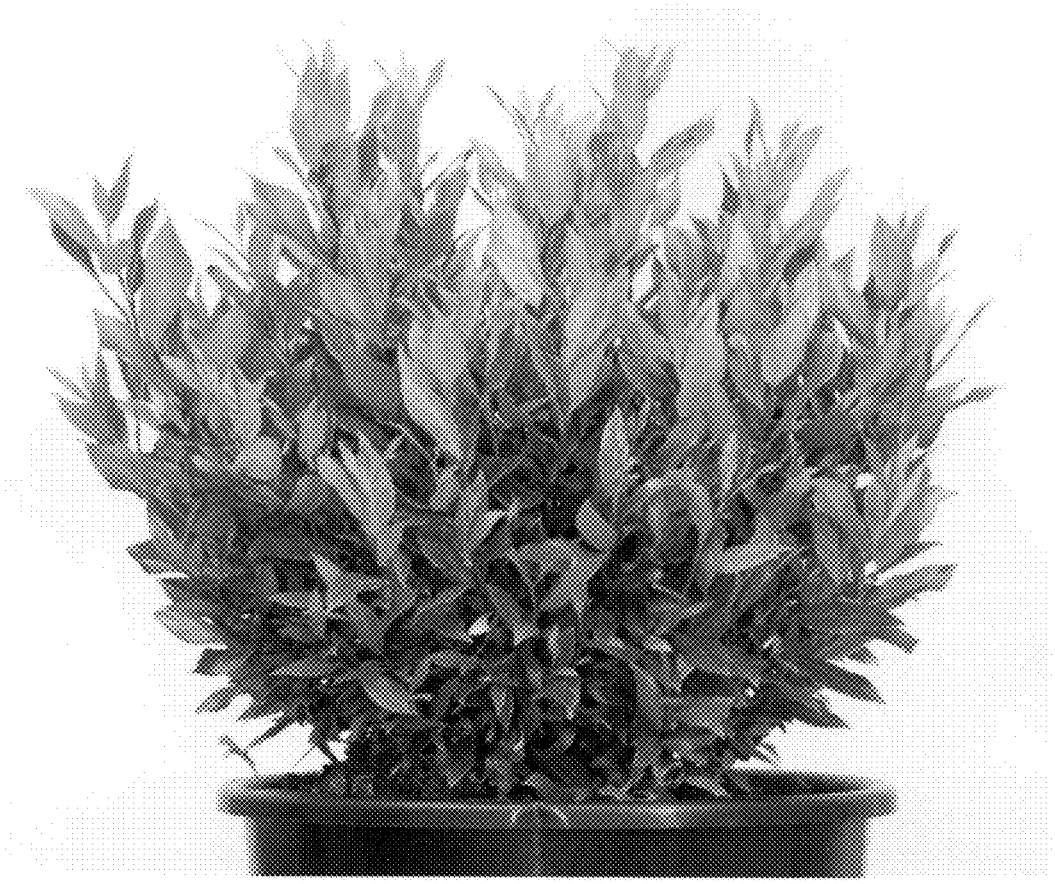
Figure 2:
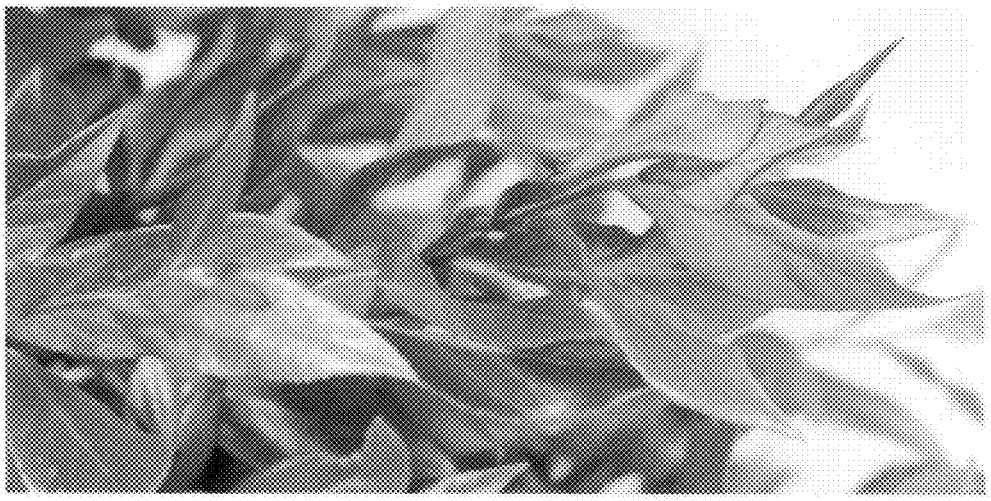

The photograph in FIG. 2 provides a close-up view a branch of 'Little Flames' and illustrates the new growth characteristics.

Figure 3:
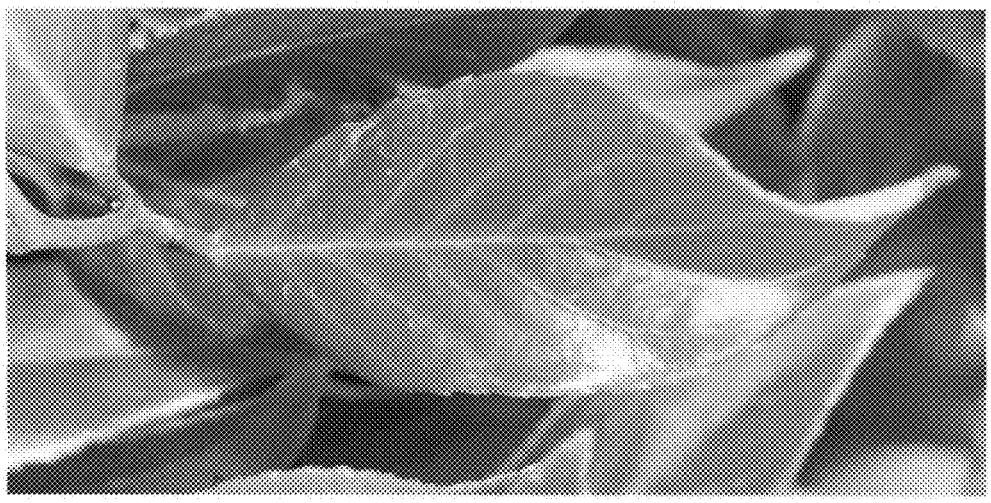

The photograph in FIG. 3 provides a close-up view of a mature leaf of 'Little Flames'.

The colors in the photograph may differ slightly from the color values cited in the detailed botanical description, which accurately describe the colors of the new *Leucothoe*.

DETAILED BOTANICAL DESCRIPTION

The following is a detailed description of 3 year-old plants of the new cultivar as grown outdoors in 12-liter containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.
*Plant habit.*—Dwarf, dense, mound of upright branches.
*Plant shape.*—Globular to broad ovate.

*Plant size.*—Reaches about 33.9 cm in height and 43.3 cm in spread.

*Cold hardiness.*—At least in U.S.D.A. Zones 5.

*Environmental stress.*—Shade tolerant.

*Plant vigor.*—Low to moderate.

*Diseases and pests.*—No susceptibility or resistance to diseases or pests has been observed.

*Root description.*—Fibrous, moderately dense.

*Propagation*.—Softwood stem cuttings.

*Growth rate.*—Low to moderate.

Stem description:

*Shape.*—Rounded.

*Stem color.*—Young branches; 180A to 181A, mature branches; 144B to 144C.

*Stem size.*—An average of 22.3 cm in length and 2 mm in diameter.

*Stem surface.*—Smooth and glossy.

*Stem aspect.*—Held at an average angle 55°.

*Branching.*—Basal branching, an average of 75 lateral branches.

Foliage description:

*Leaf shape.*—Narrow ovate to narrowly elliptic, tip typically twisted due to one large wave near the tip.

*Leaf division.*—Simple.

*Leaf base.*—Rounded.

*Leaf apex.*—Apiculate.

*Leaf fragrance.*—None.

*Leaf venation.*—Pinnate, 146D in color on upper surface, N144B in color on lower surface.

*Leaf margins.*—Finely serrate.

*Leaf arrangement.*—Alternate.

*Leaf attachment.*—Petiolate.

*Leaf surface.*—Upper surface; smooth and very glossy, lower surface; moderately glossy.

*Leaf size.*—An average of 5 cm in length and 1.9 cm in width.

*Leaf quantity.*—An average of 19 per stem.

*Leaf color.*—New growth upper surface; 180A, new growth lower surface; 177B to 177C, mature growth upper surface; between 137B and 141A, mature growth lower surface 146D.

*Petioles.*—About 5 mm in length and 1.5 mm in width and 180A in color, glossy surface.

Inflorescence description: Flowers have not been observed, expected to bloom in early spring with non-significant, small white flowers.

It is claimed:

1. A new and distinct cultivar of *Leucothoe* plant named 'Little Flames' as herein illustrated and described.

* * * * *